United States Patent
Angermann et al.

(10) Patent No.: US 11,178,868 B2
(45) Date of Patent: *Nov. 23, 2021

(54) ALKYNYL-SUBSTITUTED 3-PHENYLPYRROLIDINE-2,4-DIONES AND USE THEREOF AS HERBICIDES

(71) Applicant: Bayer CropScience Aktiengesellschaft, Monheim am Rhein (DE)

(72) Inventors: Alfred Angermann, Kriftel (DE); Stefan Lehr, Liederbach (DE); Reiner Fischer, Monheim (DE); Guido Bojack, Wiesbaden-Naurod (DE); Hendrik Helmke, Liederbach (DE); Dirk Schmutzler, Hattersheim (DE); Hansjörg Dietrich, Liederbach am Taunus (DE); Elmar Gatzweiler, Bad Nauheim (DE); Christopher Hugh Rosinger, Hofheim (DE)

(73) Assignee: Bayer CropScience Aktiengesellschaft, Monheim am Rhein (DE)

( * ) Notice: Subject to any disclaimer, the term of this patent is extended or adjusted under 35 U.S.C. 154(b) by 10 days.

This patent is subject to a terminal disclaimer.

(21) Appl. No.: 15/765,769

(22) PCT Filed: Oct. 4, 2016

(86) PCT No.: PCT/EP2016/073590
§ 371 (c)(1),
(2) Date: Apr. 4, 2018

(87) PCT Pub. No.: WO2017/060203
PCT Pub. Date: Apr. 13, 2017

(65) Prior Publication Data
US 2019/0174758 A1    Jun. 13, 2019

(30) Foreign Application Priority Data
Oct. 6, 2015  (EP) ................................ 15188613

(51) Int. Cl.
*A01N 43/36* (2006.01)
*A01N 43/38* (2006.01)
*C07D 209/54* (2006.01)

(52) U.S. Cl.
CPC ........... *A01N 43/38* (2013.01); *C07D 209/54* (2013.01)

(58) Field of Classification Search
CPC .............................. A01N 43/38; C07D 209/54
See application file for complete search history.

(56) References Cited

U.S. PATENT DOCUMENTS 8,013,172 B2    9/2011  Fischer et al.
8,410,289 B2    4/2013  Fischer et al.
8,541,617 B2    9/2013  Fischer et al.
2012/0190865 A1*  7/2012  Fischer ................ C07D 207/36
                                              548/410
2018/0170872 A1   6/2018  Angermann et al.

FOREIGN PATENT DOCUMENTS

| EP | 0355599 A1 | 2/1990 |
|---|---|---|
| EP | 0377863 A2 | 7/1990 |
| EP | 0415211 A2 | 3/1991 |
| EP | 0442077 A2 | 8/1991 |
| JP | 2000053670 A | 2/2000 |
| WO | 9625395 A1 | 8/1996 |
| WO | 9805638 A2 | 2/1998 |
| WO | 0174770 A1 | 10/2001 |
| WO | 2006000355 A1 | 1/2006 |
| WO | 2007096058 A1 | 8/2007 |
| WO | 2015/040114 A1 | 3/2015 |
| WO | 2015032702 A1 | 3/2015 |
| WO | WO2015/040114 * | 3/2015 |
| WO | 2016/207097 A1 | 12/2016 |

* cited by examiner

OTHER PUBLICATIONS

International Search Report of International Patent Application No. PCT/EP2016/073590 dated Dec. 1, 2016.

*Primary Examiner* — David Browe
(74) *Attorney, Agent, or Firm* — McBee Moore & Vanik, IP, LLC

(57) ABSTRACT

The present invention relates to alkynyl-substituted N-phenylpyrrolidine-2,4-diones according to the general formula (I) or agrochemically acceptable salts thereof, (I)

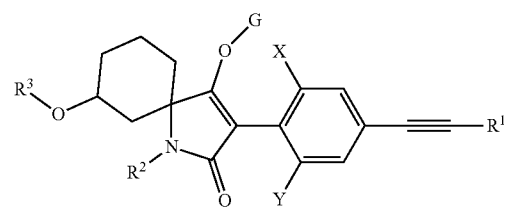

where $X=C_1-C_4$-alkyl, $C_1-C_4$-haloalkyl or $C_3-C_6$-cycloalkyl, $Y=C_1-C_4$-alkyl or $C_3-C_6$-cycloalkyl, $R^1$=hydrogen, $C_1-C_6$-alkyl, or $C_3-C_6$-cycloalkyl, $R^2$=hydrogen or methyl, $R^3=C_1-C_6$-alkyl or $C_1-C_6$-alkoxy-$C_2-C_6$-alkyl, G=hydrogen, a cleavable group L or a cation E. The invention further relates to a herbicidal composition comprising a compound of the general formula (I) and to the use of the compounds according to the invention for controlling weeds and weed grasses in crops of useful plants.

13 Claims, No Drawings

ALKYNYL-SUBSTITUTED 3-PHENYLPYRROLIDINE-2,4-DIONES AND USE THEREOF AS HERBICIDES

The present invention relates to novel herbicidally effective alkynyl-substituted 3-phenylpyrrolidine-2,4-diones according to the general formula (I) or agrochemically acceptable salts thereof, and to the use thereof for controlling weeds and weed grasses in crops of useful plants.

DESCRIPTION OF RELATED ART

The compound class of 3-arylpyrrolidine-2,4-diones and their preparation and use as herbicides are well known from the prior art. Moreover, bicyclic 3-arylpyrrolidine-2,4-dione derivatives (EP-A-355 599, EP-A-415 211 and JP-A 12-053 670 ff.) and substituted monocyclic 3-arylpyrrolidine-2,4-dione derivatives (EP-A-377 893 and EP-A-442 077 ff.) with a herbicidal, insecticidal or fungicidal effect are also described.

Alkynyl-substituted 3-phenylpyrrolidine-2,4-diones with a herbicidal effect are also known from WO 96/82395, WO 98/05638, WO 01/74770, WO 14/032702 or WO15/040114.

The effectiveness of these herbicides against harmful plants is dependent on numerous parameters, for example on the application rate used, the preparation form (formulation), the harmful plants to be controlled in each case, the spectrum of harmful plants, the climate and soil proportions, as well as the action time and/or the rate of degradation of the herbicide. In order to develop a sufficient herbicidal effect, numerous herbicides from the group of 3-arylpyrrolidine-2,4-diones require high application rates and/or narrow spectra of harmful plants, which makes their application economically unattractive. There is therefore the need for alternative herbicides which have improved properties and are economically attractive and simultaneously efficient.

SUMMARY

Consequently, the object of the present invention is to provide novel compounds which do not have the stated disadvantages.

The present invention therefore relates to novel alkynyl-substituted N-phenylpyrrolidine-2,4-diones of the general formula (I),

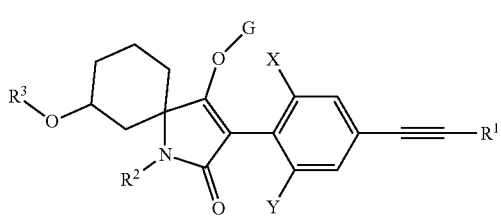

(I)

or an agrochemically acceptable salt thereof,
where
X=$C_1$-$C_4$-alkyl, $C_1$-$C_4$-haloalkyl or $C_3$-$C_6$-cycloalkyl,
Y=$C_1$-$C_4$-alkyl or $C_3$-$C_6$-cycloalkyl,
$R^1$=hydrogen, $C_1$-$C_6$-alkyl, or $C_3$-$C_6$-cycloalkyl,
$R^2$=hydrogen or methyl,
$R^3$=$C_1$-$C_6$-alkyl or $C_1$-$C_6$-alkoxy-$C_2$-$C_6$-alkyl,
G=hydrogen, a cleavable group L or a cation E; where
  L=one of the following radicals

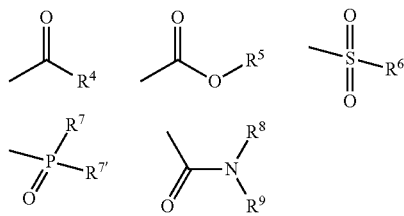

in which
$R^4$=$C_1$-$C_4$-alkyl or $C_1$-$C_3$-alkoxy-$C_1$-$C_4$-alkyl,
$R^5$=$C_1$-$C_4$-alkyl,
$R^6$=$C_1$-$C_4$-alkyl, an unsubstituted phenyl or a phenyl substituted one or more times with halogen, $C_1$-$C_4$-alkyl, $C_1$-$C_4$-haloalkyl, $C_1$-$C_4$-alkoxy, $C_1$-$C_4$-haloalkoxy, nitro or cyano,
$R^7$, $R^{7'}$=independently of one another methoxy or ethoxy,
$R^8$ and $R^9$=in each case independently of one another methyl, ethyl, phenyl or together form a saturated 5-, 6- or 7-membered ring, or together form a saturated 5-, 6- or 7-membered heterocycle with an oxygen or sulphur atom,
E=an alkali metal ion, an ion equivalent of an alkaline earth metal, an ion equivalent of aluminium or an ion equivalent of a transition metal, a magnesium halogen cation, or
  an ammonium ion, in which optionally one, two, three or all four hydrogen atoms by identical or different radicals from the groups hydrogen, $C_1$-$C_5$-alkyl, $C_1$-$C_5$-alkoxy or $C_3$-$C_7$-cycloalkyl, which can in each case be substituted one or more times with fluorine, chlorine, bromine, cyano, hydroxy or be interrupted by one or more oxygen or sulphur atoms, or
  a cyclic secondary or tertiary aliphatic or heteroaliphatic ammonium ion, for example morpholinium, thiomorpholinium, piperidinium, pyrrolidinium, or in each case protonated 1,4-diazabicyclo[1.1.2]octanes (DABCO) or 1,5-diazabicyclo[4.3.0]undec-7-ene (DBU), or
  a heterocyclic ammonium cation, for example in each case protonated pyridine, 2-methylpyridine, 3-methylpyridine, 4-methylpyridine, 2,4-dimethylpyridine, 2,5-di-methylpyridine, 2,6-dimethylpyridine, 5-ethyl-2-methylpyridine, pyrrole, imidazole, quinoline, quinoxaline, 1,2-dimethylimidazole, 1,3-dimethylimidazolium methyl sulphate, or furthermore is a sulphonium ion.

DETAILED DESCRIPTION OF A PREFERRED EMBODIMENT

A general definition of the compounds of the invention is provided by the formula (I). Preferred substituents or ranges of the radicals given in the formulae mentioned above and below are illustrated hereinafter:

In the formula (I) and all the formulae which follow, alkyl radicals having more than two carbon atoms may be straight-chain or branched. Alkyl radicals are e.g. methyl, ethyl, n- or isopropyl, n-, iso, t- or 2-butyl, pentyls such as n-pentyl, 2,2,-dimethylpropyl and 3-methylbutyl. Cycloalkyl is a carbocyclic saturated ring system having three to six carbon atoms, for example cyclopropyl, cyclobutyl, cyclopentyl or cyclohexyl.

Halogen is fluorine, chlorine, bromine or iodine.

The compounds of the formula (I) can, depending on the type of substituents, be present as geometric and/or optical isomers or isomer mixtures, in differing composition, for example also in cis or trans form, which are defined as follows:

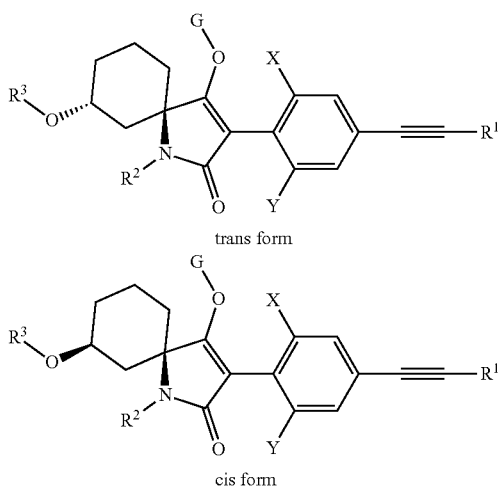

trans form cis form

The isomer mixtures which may arise in the synthesis can be separated by the conventional technical methods.

Both the pure isomers and also the tautomer and isomer mixtures, their preparation and use, as well as compositions comprising these are provided by the present invention. However, for the sake of simplicity, the terminology used hereinbelow is compounds of the formula (I) although both the pure compounds and also optionally mixtures with different proportions of isomeric and tautomeric compounds are intended.

Preference is given to compounds in which
X=$C_1$-$C_4$-alkyl or $C_3$-$C_6$-cycloalkyl,
Y=$C_1$-$C_4$-alkyl or $C_3$-$C_6$-cycloalkyl,
$R^1$=hydrogen, methyl, ethyl, isopropyl or cyclopropyl,
$R^2$=hydrogen or methyl,
$R^3$=$C_1$-$C_6$-alkyl or $C_1$-$C_4$-alkoxy-$C_2$-$C_4$-alkyl,
G=hydrogen, a cleavable group L or a cation E in which
    L=one of the following radicals

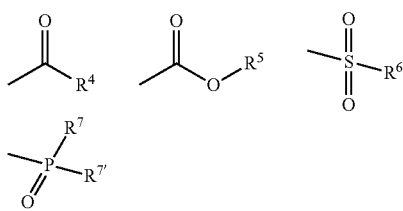

in which
$R^4$=$C_1$-$C_4$-alkyl,
$R^5$=$C_1$-$C_4$-alkyl,
$R^6$=$C_1$-$C_4$-alkyl, an unsubstituted phenyl or a phenyl substituted with halogen, $C_1$-$C_4$-alkyl or $C_1$-$C_4$-alkoxy,
$R^7$, $R^{7'}$=independently of one another methoxy or ethoxy, E=an alkali metal ion, an ion equivalent of an alkaline earth metal, an ion equivalent of aluminium or an ion equivalent of a transition metal, or an ammonium ion in which optionally one, two, three or all four hydrogen atoms by identical or different radicals from the groups hydrogen or $C_1$-$C_5$-alkyl, or a tertiary aliphatic or heteroaliphatic ammonium ion, or a heterocyclic ammonium cation, for example in each case protonated pyridine, quinoline, quinoxaline, 1,2-dimethylimidazole, 1,3-dimethylimidazolium methyl sulphate, or also is a sulphonium ion.

Particular preference is given to compounds of the general formula (I) in which
X=methyl, ethyl or cyclopropyl,
Y=methyl or ethyl,
$R^1$=hydrogen, methyl, ethyl, isopropyl or cyclopropyl,
$R^2$=hydrogen
$R^3$=$C_1$-$C_4$-alkyl or $C_1$-$C_3$-alkoxy-$C_2$-$C_4$-alkyl,
G=hydrogen, a cleavable group L or a cation E in which
    L=one of the following radicals

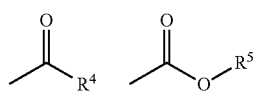

in which
$R^4$=$C_1$-$C_4$-alkyl,
$R^5$=$C_1$-$C_4$-alkyl,
E=an alkali metal ion, an ion equivalent of an alkaline earth metal, an ion equivalent of aluminium, an ion equivalent of a transition metal or is a magnesium halogen cation, a tetra-$C_1$-$C_5$-alkyl ammonium cation or a heterocyclic ammonium cation, for example in each case protonated pyridine or quinoline.

Very particular preference is given to compounds of the formula (I) in which
X=methyl or ethyl,
Y=methyl or ethyl,
$R^1$=hydrogen, methyl, ethyl or cyclopropyl,
$R^2$=hydrogen,
$R^3$=$C_1$-$C_4$-alkyl or $C_1$-$C_3$-alkoxy-$C_2$-$C_4$-alkyl,
G=hydrogen, a cleavable group L or a cation E in which
    L=one of the following radicals

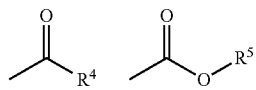

in which
$R^4$=methyl, ethyl or isopropyl,
$R^5$=methyl, ethyl or isopropyl,
E=a sodium, potassium, trimethylammonium, pyridinium, quinolinium or trimethylsulphonium cation or an ion equivalent of calcium or magnesium.

For illustration, the following compounds according to the invention may be specifically mentioned:

TABLE 1

Example numbers 1.01-1.42 where $R^1$ = H

| Example No. | $R^3$ | X | Y |
|---|---|---|---|
| 1.01 | Me | H | Me |
| 1.02 | Me | H | Et |
| 1.03 | Me | Me | Me |
| 1.04 | Me | Me | Et |
| 1.05 | Me | Et | Et |
| 1.06 | Me | cyclopropyl | Me |
| 1.07 | Me | cyclopropyl | Et |
| 1.08 | Et | H | Me |
| 1.09 | Et | H | Et |
| 1.10 | Et | Me | Me |
| 1.11 | Et | Me | Et |
| 1.12 | Et | Et | Et |
| 1.13 | Et | cyclopropyl | Me |
| 1.14 | Et | cyclopropyl | Et |
| 1.15 | n-propyl | H | Me |
| 1.16 | n-propyl | H | Et |
| 1.17 | n-propyl | Me | Me |
| 1.18 | n-propyl | Me | Et |
| 1.19 | n-propyl | Et | Et |
| 1.20 | n-propyl | cyclopropyl | Me |
| 1.21 | n-propyl | cyclopropyl | Et |
| 1.22 | isopropyl | H | Me |
| 1.23 | isopropyl | H | Et |
| 1.24 | isopropyl | Me | Me |
| 1.25 | isopropyl | Me | Et |
| 1.26 | isopropyl | Et | Et |
| 1.27 | isopropyl | cyclopropyl | Me |
| 1.28 | isopropyl | cyclopropyl | Et |
| 1.29 | n-butyl | H | Me |
| 1.30 | n-butyl | H | Et |
| 1.31 | n-butyl | Me | Me |
| 1.32 | n-butyl | Me | Et |
| 1.33 | n-butyl | Et | Et |
| 1.34 | n-butyl | cyclopropyl | Me |
| 1.35 | n-butyl | cyclopropyl | Et |
| 1.36 | $CH_3OCH_2CH_2O-$ | H | Me |
| 1.37 | $CH_3OCH_2CH_2O-$ | H | Et |
| 1.38 | $CH_3OCH_2CH_2O-$ | Me | Me |
| 1.39 | $CH_3OCH_2CH_2O-$ | Me | Et |
| 1.40 | $CH_3OCH_2CH_2O-$ | Et | Et |
| 1.41 | $CH_3OCH_2CH_2O-$ | cyclopropyl | Me |
| 1.42 | $CH_3OCH_2CH_2O-$ | cyclopropyl | Et |

TABLE 2

Example numbers 2.01-2.42 where $R^1$ = $CH_3$

Example numbers 2.01-2.42, where $R^3$, X and Y are identical to those in Table 1

TABLE 3

Example numbers 3.01-3.42 where $R^1$ = $C_2H_5$

Example numbers 3.01-3.42, where $R^3$, X and Y are identical to those in Table 1

TABLE 4

Example numbers 4.01-4.42 where $R^1$ = $nC_3H_7$

Example numbers 4.01-4.42, where $R^3$, X and Y are identical to those in Table 1

TABLE 5

Example numbers 5.01-5.42 where $R^1$ = isopropyl

Example numbers 5.01-5.42, where $R^3$, X and Y are identical to those in Table 1

TABLE 6

Example numbers 6.01-6.42 where $R^1$ = cyclopropyl

Example numbers 6.01-6.42, where $R^3$, X and Y are identical to those in Table 1

The preparation of the compounds according to the invention of the general formula (I) can take place in accordance with processes known in the literature, for example by
a) cyclizing a compound of the general formula (II)

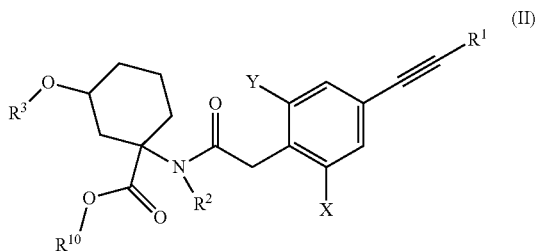
(II)

in which X, Y, $R^1$, $R^2$ and $R^3$ have the meanings given above, and $R^{10}$ is alkyl, preferably methyl or ethyl, optionally in the presence of a suitable solvent or diluent, with a suitable base with formal cleaving off of the group $R^{10}OH$, or
b) reacting a compound of the general formula (Ia),

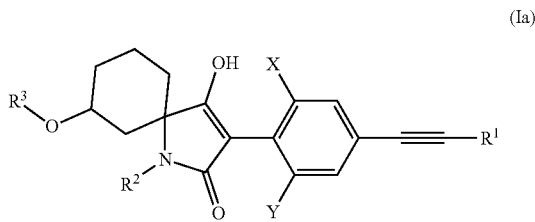
(Ia)

in which X, Y, $R^1$, $R^2$ and $R^3$ have the meanings given above, with a compound of the general formula (III), Hal-L (III)

in which L has the meaning given above and Hal is a halogen, preferably chlorine or bromine or can be a sulphonic acid group, optionally in the presence of a suitable solvent or diluent, and also a suitable base,
(c) by reacting compounds of the general formula (IV),

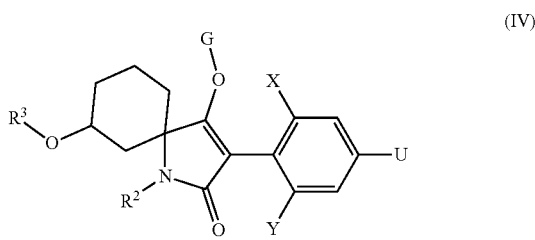
(IV)

in which X, Y, $R^2$ and $R^3$ and G have the meanings given above, and U is a suitable leaving group such as, for example, bromine, iodine, triflate or nonaflate, with a suitable alkynyl reagent of the general formula (V),

(V)

in which $R^1$ has the meaning given above and W is hydrogen or a suitable leaving group, optionally in the presence of a suitable catalyst and a suitable base. Suitable leaving groups W are, for example, halogen atoms such as chlorine, bromine or iodine, alkylsulphonic ester groups such as, for example, triflate, mesylate or nonaflate, magnesium chloride, zinc chloride, a trialkyltin radical, carboxyl and boric acid radicals such as $—B(OH)_2$ or $—B(Oalkyl)_2$. $Pd^0$ complexes in particular are very readily suitable as catalysts, where in many cases also the addition of $Cu^{(I)}$ salts may be very advantageous.

The described methodology is known in the literature in the prior art and moreover in this connection also under the keyword "palladium-catalysed cross-coupling", "Sonogashira-, Negishi-, Suzuki-, Stille- or Kumada coupling".

Alternatively, a compound of the general formula (IV) can also be reacted with an alkynyl reagent of the general formula (VI) in an analogous application of the coupling methodology described above, then cleaved into ethynyl compounds of the general formula (VIII) and these are finally converted with a suitable alkylating reagent to the compound (I) according to the invention, where in each case X, Y, $R^1$, $R^2$, $R^3$, G, U and W have the described meaning and the cleavable group $R^{11}$ can be for example a group $(C_1-C_4-alkyl)_2C—OH$ or else trimethylsilyl.

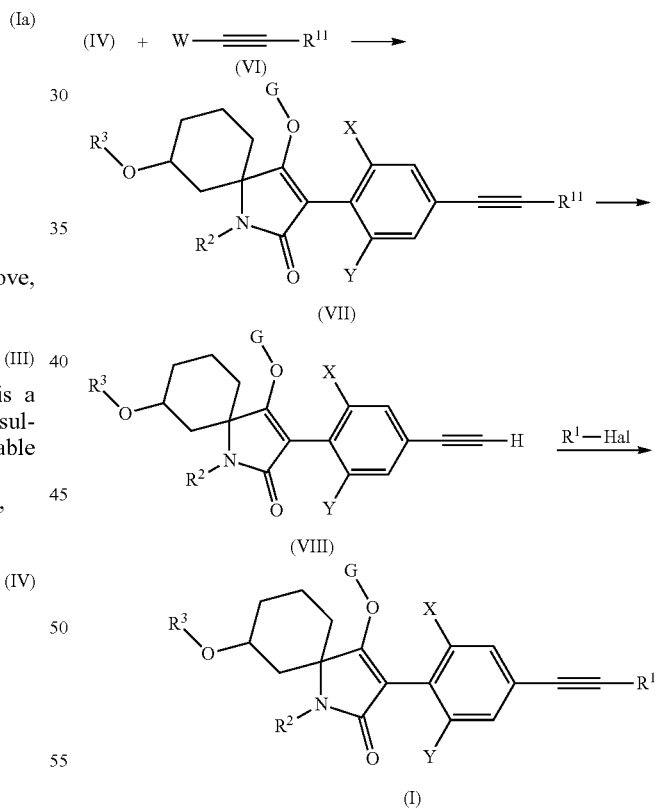

This technology, likewise known in the literature, is explained in more detail for example in Beilstein *Journal of Organic Chemistry* 2011, 7(55), 426-431 and *Catalysis Communications* 2015, 60, 82-87.

If the radical $R^1$ in the general formula (I) is methyl and X, Y, $R^2$, $R^3$ and G, U and W have the meaning described further above, a further alternative consists in reacting a compound of the general formula (IV) with an alkynyl reagent of the general formula (IX), in which $R^{12}$ for example is a $C_1$-$C_4$-trialkylsilyl radical and W has the meaning given above, in an analogous application of the above-described coupling methodology to give a compound of the general formula (X). The group $R^{12}$ can then be cleaved off under suitable conditions, giving compounds according to the invention of the formula (I) where $R^3$=Me.

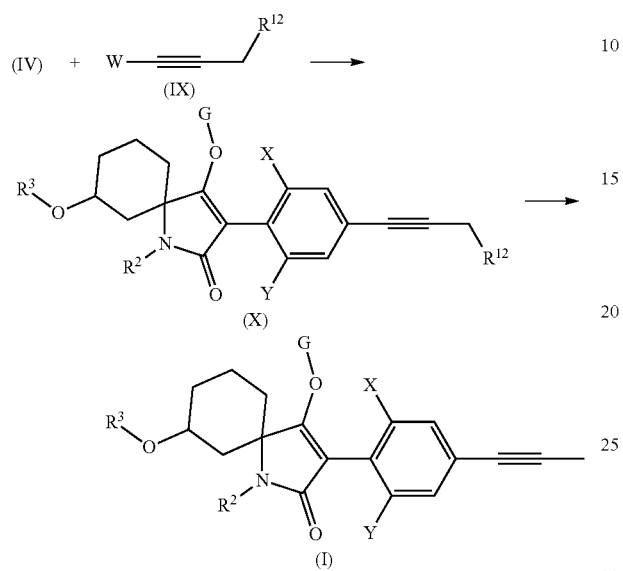

This technology, known in the literature, is described for example in the *Journal of Medicinal Chemistry* 2007, 50 (7), 1627-1634.

The required precursors of the general formula (II)

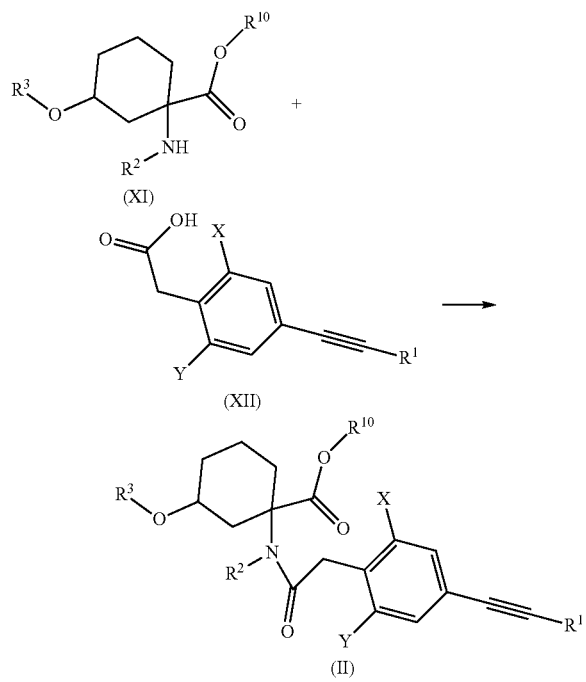

can be prepared analogously to known processes, for example by reacting an amino acid ester of the general formula (XI) with a phenyl acetic acid of the general formula (XII), in which X, Y, $R^1$, $R^2$ and $R^3$ and $R^{10}$ have the above-described meaning, optionally by adding a water-withdrawing agent and optionally in the presence of a suitable solvent or diluent.

A further variant for preparing precursors of the general formula (II) consists, inter alia, also in reacting a compound with the general formula (XIII), in which X, Y, $R^2$, $R^3$, $R^{10}$ and U have the meaning given above, with a compound of the general formula (V) or (VI), in which W, $R^3$ and $R^{11}$ have the meaning given above, by the cross-coupling methodology already described:

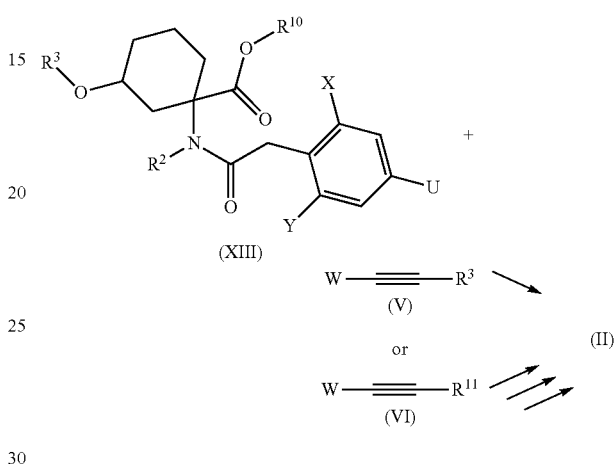

Phenyl acetic acids of the general formula (VII)—namely 2,6-dimethyl-4-propargylphenyl acetic acid—are mentioned in principle in WO 2015/040114, but no access route to these compounds is described.

However, they can be prepared in accordance with processes known in the literature, for example by reacting a compound with the general formula (X), where X, Y, U are as defined above and R=$C_1$-$C_4$-alkyl, again with technology already described above with reagents of the general formula (V) or (V), where W, $R^1$ and $R^{11}$ are as defined above.

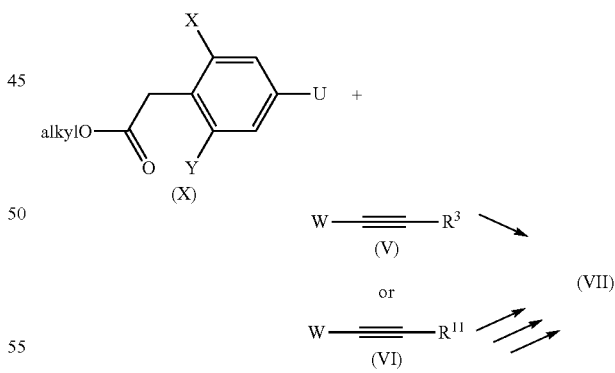

The compounds according to the invention of the formula (I) and/or salts thereof, referred to hereinbelow together as "compounds according to the invention", have an excellent herbicidal effectiveness against a broad spectrum of economically important mono- and dikotyledonous annual weeds. The active ingredients also act efficiently on perennial weeds which produce shoots from rhizomes, root stocks and other perennial organs and which are difficult to control.

The present invention therefore also provides a method for controlling unwanted plants or for regulating the growth of plants, preferably in plant crops, in which one or more compound(s) according to the invention is/are applied to the plants (for example harmful plants such as monocotyledonous or dicotyledonous weeds or unwanted crop plants), the seed (for example grains, seeds or vegetative propagules such as tubers or shoot parts with buds) or the area on which the plants grow (for example the area under cultivation). The compounds of the invention can be deployed, for example, prior to sowing (if appropriate also by incorporation into the soil), prior to emergence or after emergence. Specifically, mention may be made, by way of example, to a number of mono- and dicotyledonous weed flora which can be controlled by the compounds according to the invention, without any intention of limitation to certain varieties by virtue of the naming.

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

If the compounds of the invention are applied to the soil surface before germination, either the emergence of the weed seedlings is prevented completely or the weeds grow until they have reached the cotyledon stage, but then they stop growing and ultimately die completely after three to four weeks have passed.

If the active ingredients are applied post-emergence to the green parts of the plants, growth stops after the treatment, and the harmful plants remain at the growth stage at the time of application, or they die completely after a certain time, such that competition by the weeds, which is harmful to the crop plants, is thus eliminated very early and in a lasting manner.

Although the compounds according to the invention have an excellent herbicidal activity towards mono- and dicotyledonous weeds, crop plants of economically important crops e.g. dicotyledonous crops of the genera *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia*, or monocotyledonous crops of the genera *Allium, Ananas, Asparagus, Avena, Hordeum, Oryza, Panicum, Saccharum, Secale, Sorghum, Triticale, Triticum, Zea*, in particular *Zea* and *Triticum*, are damaged only insignificantly, or not at all, depending on the structure of the particular compound according to the invention and its application rate. For these reasons, the present compounds are very suitable for selective control of unwanted plant growth in plant crops such as agriculturally useful plants or ornamental plants.

In addition, the compounds according to the invention (depending on their particular structure and the application rate deployed) have outstanding growth-regulating properties in crop plants. They intervene in the plants' own metabolism with regulatory effect, and can thus be used for controlled influencing of plant constituents and to facilitate harvesting, for example by triggering desiccation and stunted growth. Furthermore, they are also suitable for the general control and inhibition of unwanted vegetative growth without killing the plants in the process. An inhibition of the vegetative growth plays a large role in many mono- and dicotyledonous crops since, for example, the storage formation can be reduced or completely prevented as a result.

By virtue of their herbicidal and plant growth regulatory properties, the active ingredients can also be used to control harmful plants in crops of genetically modified plants or plants modified by conventional mutagenesis. In general, transgenic plants are characterized by particular advantageous properties, for example by resistances to certain pesticides, in particular certain herbicides, resistances to plant diseases or pathogens of plant diseases, such as certain insects or microorganisms such as fungi, bacteria or viruses. Other particular properties relate, for example, to the harvested material with regard to quantity, quality, storability, composition and specific constituents. For instance, there are known transgenic plants with an elevated starch content or altered starch quality, or those with a different fatty acid composition in the harvested material.

As regards transgenic crops, preference is given to the application of the compounds according to the invention in economically important transgenic crops of useful plants and ornamental plants, e.g. of cereals such as wheat, barley, rye, oats, millet, rice, maniok and corn or else crops of sugar cane, cotton, soybean, rapeseed, potatoes, tomatoes, peas and other vegetable varieties. Preferably, the compounds of the invention can be used as herbicides in crops of useful plants which are resistant, or have been made resistant by genetic engineering, to the phytotoxic effects of the herbicides.

Conventional ways of producing novel plants which have modified properties in comparison to existing plants consist, for example, in traditional cultivation methods and the generation of mutants. Alternatively, novel plants with modified properties can be generated with the aid of recombinant methods (see, for example, EP-A-0221044, EP-A-0131624). For example, there have been descriptions in several cases of:

genetic modifications of crop plants for the purpose of modifying the starch synthesized in the plants (e.g. WO 92/11376, WO 92/14827, WO 91/19806), transgenic crop plants which are resistant to certain herbicides of the glufosinate type (cf. e.g. EP A-0242236, EP-A-242246) or glyphosate type (WO 92/00377) or the sulphonylurea type (EP-A-0257993, USA 5013659), transgenic crop plants, for example cotton, with the ability to produce *Bacillus thuringiensis* toxins (Bt toxins), which make the plants resistant to particular pests (EP-A-0142924, EP-A-0193259), transgenic crop plants with a modified fatty acid composition (WO 91/13972), genetically modified crop plants with novel constituents or secondary metabolites, for example novel phytoalexins, which bring about an increased disease resistance (EPA 309862, EPA0464461), genetically modified plants having reduced photorespiration, which have higher yields and higher stress tolerance (EPA 0305398), transgenic crop plants which produce pharmaceutically or diagnostically important proteins ("molecular pharming"), transgenic crop plants which feature higher yields or better quality, transgenic crop plants which are characterized by a combination e.g. of the aforementioned new properties ("gene stacking").

Numerous molecular biology techniques which can be used to produce novel transgenic plants with modified properties are known in principle; see, for example, I. Potrykus and G. Spangenberg (eds.) Gene Transfer to Plants, Springer Lab Manual (1995), Springer Verlag Berlin, Heidelberg, or Christou, "Trends in Plant Science" 1 (1996) 423-431).

For such recombinant manipulations, nucleic acid molecules which allow mutagenesis or sequence alteration by recombination of DNA sequences can be introduced into plasmids. With the aid of standard methods, it is possible, for example, to undertake base exchanges, remove parts of sequences or add natural or synthetic sequences.

To join the DNA fragments with one another, adapters or linkers can be placed onto the fragments, see e.g. Sambrook et al., 1989, Molecular Cloning, A Laboratory Manual, 1st edition Cold Spring Harbor Laboratory Press, Cold Spring Harbor, N.Y., or Winnacker "Gene and Klone [Genes and clones]", VCH Weinheim 1st edition 1996.

For example, the generation of plant cells with a reduced activity of a gene product can be achieved by expressing at least one corresponding antisense RNA, a sense RNA for achieving a cosuppression effect, or by expressing at least one suitably constructed ribozyme which specifically cleaves transcripts of the abovementioned gene product. To this end, it is firstly possible to use DNA molecules which encompass the entire coding sequence of a gene product inclusive of any flanking sequences which may be present, and also DNA molecules which only encompass portions of the coding sequence, in which case it is necessary for these portions to be long enough to have an antisense effect in the cells. It is also possible to use DNA sequences which have a high degree of homology to the coding sequences of a gene product, but are not completely identical to them.

When expressing nucleic acid molecules in plants, the protein synthesized may be localized in any desired compartment of the plant cell. However, to achieve localization in a particular compartment, it is possible, for example, to join the coding region to DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give rise to entire plants. In principle, the transgenic plants may be plants of any desired plant species, i.e. not only monocotyledonous but also dicotyledonous plants.

Thus, transgenic plants can be obtained whose properties are altered by overexpression, suppression or inhibition of homologous (=natural) genes or gene sequences or expression of heterologous (=foreign) genes or gene sequences.

The compounds of the invention can be used with preference in transgenic crops which are resistant to growth regulators, for example dicamba, or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of the sulphonylureas, the glyphosates, glufosinates or benzoylisoxazoles and analogous active ingredients.

When the active ingredients of the invention are used in transgenic crops, not only do the effects toward harmful plants which are observed in other crops occur, but often also effects which are specific to application in the particular transgenic crop, for example an altered or specifically widened spectrum of weeds which can be controlled, altered application rates which can be used for the application, preferably good combinability with the herbicides to which the transgenic crop is resistant, and influencing of growth and yield of the transgenic crop plants.

The invention therefore also provides for the use of the compounds of the invention as herbicides for control of harmful plants in transgenic crop plants.

In a preferred embodiment of the present invention, the compounds of the general formula (I) can also be used to control those harmful plants e.g. from the group *Agrostis, Alopecurus, Apera, Avena, Brachiaria, Bromus, Cenchrus, Digitaria, Echinochloa, Eleusine, Eriochloa, Leptochloa, Lolium, Ottochloa, Panicum, Pennisetum, Phalaris, Poa, Rottboellia, Setaria* and/or *Sorghum* weeds; in particular *Alopecurus, Apera, Avena, Brachiaria, Bromus, Digitaria, Echinochloa, Eriochloa, Lolium, Panicum, Phalaris, Poa, Setaria* and/or *Sorghum* weeds, which are resistant to one or more herbicides inhibiting the enzyme acetyl-CoA-carboxylase (ACCase). ACCase-inhibiting herbicides are, inter alia, pinoxaden, clodinafop-propargyl, fenoxaprop-P-ethyl, diclofop-methyl, fluazifop-P-butyl, haloxyfop-P-methyl, quizalofop-P-ethyl, propaquizafop, cyhalofop-butyl, clethodim, sethoxydim, cycloxydim, tralkoxydim or butroxydim, and/or are resistant to glyphosate, and/or are resistant to one or more herbicides inhibiting the acetolactate synthase (ALS), such as, for example, one or more sulphonylurea herbicides (e.g. iodosulphurone-methyl, mesosulphurone-methyl, tribenuron-methyl, triasulphurone, prosulphurone, sulphosulphurone, pyrazosulphurone-ethyl, bensulphurone-methyl, nicosulphurone, flazasulphurone, iofensulphurone, metsulphurone-methyl, or any other sulphonylurea disclosed in the "The Pesticide Manual", 15th edition (2009) or 16th edition (2012), C.D.S. Tomlin, British Crop Protection Council, and/or one or more triazolo-pyrimidine herbicides (e.g. florasulam, pyroxsulam or penoxsulam) and/or one or more pyrimidinyl (thio or oxy) benzoate herbicides (e.g. bispyribac-sodium or pyriftalid) and/or one or more sulphonylamino-carbonyltriazolinone herbicides (e.g. thiencarbazone-methyl, propoxycarbazone-sodium or flucarbazone-sodium) and/or imidazolinone herbicides (e.g. imazamox).

Specific examples of such harmful grasses resistant to ACCase and/or ALS inhibitors and/or glyphosate are, inter alia, *Alopecurus myosuroides, Apera spica-venti, Avena fatua, Avena sterilis, Brachiaria decumbens, Brachiaria plantaginea, Digitatia horizontalis, Digitaria insularis, Digitaria sanguinalis, Echinochloa colona, Echinochloa crus-galli, Eleusine indica, Lolium multiflorum, Lolium rigidum, Lolium perenne, Phalaris minor, Phalaris paradoxa, Setaria viridis, Setaria faberi* or *Setaria glauca.*

In a particularly preferred embodiment of the present invention, the compounds according to the invention of the general formula (I) can be used against harmful plants which are resistant to one or more ACCase inhibiting herbicides (e.g. selected from the above list) or are indeed at least partially on account of mutations (e.g. substitution) of one or more amino acids in the ACCase target site of the harmful plant (cf. e.g. S. B. Powles and Qin Yu, "Evolution in Action: Plants Resistant to Herbicides", Annu. Rev. Plant Biol., 2010, 61, p. 317-347); and/or which are resistant to glyphosate, and indeed at least partly on account of mutation (e.g. substitution) of one or more amino acids at the EPSPS target site in the weed in question to which glyphosate is directed; and/or which are resistant to one or more ALS-inhibiting herbicides (e.g. selected from the above list of ALS-inhibiting herbicides) and indeed at least partly on account of mutations (e.g. substitution) of one or more amino acids in the ALS target site in the weed in question (cf. e.g. S. B. Powles and Qin Yu, "Evolution in Action: Plants Resistant to Herbicides", Annu. Rev. Plant Biol., 2010, 61, p. 317-347); and/or which are resistant to one or more ACCase inhibiting herbicides (e.g. selected from the above list) and/or to glyphosate and/or to one or more ALS-inhibiting herbicides (e.g. selected from the above list) and indeed at least partially through a metabolically induced herbicide resistance, e.g. at least partially due to a cytochrome P450-mediated metabolism (cf. e.g. S. B. Powles and Qin Yu, "Evolution in Action: Plants Resistant to Herbicides", Annu. Rev. Plant Biol., 2010, 61, p. 317-347).

The compounds according to the invention exhibit superior properties compared to the compounds from the prior art, for example WO 2015/040114, compound 41.03 (see also the comparison data in Tables 9 and 10).

The compounds of the invention can be applied in the form of wettable powders, emulsifiable concentrates, sprayable solutions, dusting products or granules in the customary formulations. The invention therefore also provides herbicidal and plant-growth-regulating compositions which comprise the compounds of the invention.

The compounds according to the invention can be formulated in various ways according to which biological and/or chemical physical parameters are pregiven. Possible formulations include, for example: Wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), dispersions based on oil or water, oil-miscible solutions, capsule suspensions (CS), dusting products (DP), dressings, granules for scattering and soil application, granules (GR) in the form of micro granules, spray granules, absorption and adsorption granules, water-dispersible granules (WG), water-soluble granules (SG), ULV formulations, microcapsules and waxes. These individual formulation types are known in principle and are described, for example, in: Winnacker Kuchler, "Chemische Technologie [Chemical Technology]", Volume 7, C. Hanser Verlag Munich, 4th Ed. 1986, Wade van Valkenburg, "Pesticide Formulations", Marcel Dekker, N.Y., 1973, K. Martens, "Spray Drying" Handbook, 3rd Ed. 1979, G. Goodwin Ltd. London.

The formulation auxiliaries required, such as inert materials, surfactants, solvents and further additives, are likewise known and are described, for example, in: Watkins, "Handbook of Insecticide Dust Diluents and Carriers", 2nd ed., Darland Books, Caldwell N.J.; H. v. Olphen, "Introduction to Clay Colloid Chemistry", 2nd ed., J. Wiley & Sons, N.Y.; C. Marsden, "Solvents Guide", 2nd ed., Interscience, N.Y. 1963; McCutcheon's "Detergents and Emulsifiers Annual", MC Publ. Corp., Ridgewood N.J., Sisley and Wood, "Encyclopedia of Surface Active Agents", Chem. Publ. Co. Inc., N.Y. 1964, Schönfeldt, "Grenzflächenaktive Äthylenoxidaddukte [Interface-active ethylene oxide adducts]", Wiss. Verlagsgesell., Stuttgart 1976, Winnacker Küchler, "Chemische Technologie [Chemical Technology]", Volume 7, C. Hanser Verlag Munich, 4th Ed. 1986.

On the basis of these formulations, it is also possible to produce combinations with other pesticidally active substances, for example insecticides, acaricides, herbicides, fungicides, and also with safeners, fertilizers and/or growth regulators, for example in the form of a finished formulation or as a tankmix. Suitable safeners are e.g. mefenpyr-diethyl, cyprosulphamide, isoxadifen-ethyl, cloquintocet-mexyl and dichlormid.

Wettable powders are preparations uniformly dispersible in water which, alongside the active ingredient apart from a diluent or inert substance, also comprise surfactants of an ionic and/or non-ionic type (wetting agent, dispersant), e.g. polyoxyethylated alkylphenols, polyoxethylated fatty alcohols, polyoxethylated fatty amines, fatty alcohol polyglycolethersulphates, alkanesulphonates, alkylbenzenesulphonates, sodium ligninosulphonate, sodium 2,2'-dinaphthylmethane-6,6'-disulphonate, sodium dibutylnaphthalenesulphonate or else sodium oleoylmethyltaurate. To produce the wettable powders, the herbicidally active ingredients are finely ground, for example in customary apparatus such as hammer mills, blower mills and air-jet mills, and simultaneously or subsequently mixed with the formulation auxiliaries.

Emulsifiable concentrates are produced by dissolving the active ingredient in an organic solvent, for example butanol, cyclohexanone, dimethylformamide, xylene, or else relatively high-boiling aromatics or hydrocarbons or mixtures of the organic solvents, with addition of one or more ionic and/or nonionic surfactants (emulsifiers). Examples of emulsifiers which may be used are: Calcium alkylarylsulphonic acid salts such as Ca dodecylbenzenesulphonate or nonionic emulsifiers such as fatty acid polyglycol esters, alkylaryl polyglycol ethers, fatty alcohol polyglycol ethers, propylene oxide ethylene oxide condensation products, alkylpolyethers, sorbitan esters such as e.g. sorbitan fatty acid esters or polyoxyethylene sorbitan esters such as e.g. polyoxyethylene sorbitan fatty acid esters.

Dustable powders are obtained by grinding the active ingredient with finely distributed solid substances, for example talc, natural clays such as kaolin, bentonite and pyrophyllite, or diatomaceous earth.

Suspension concentrates can be based on water or oil. They can be produced, for example, by wet grinding by means of standard commercial bead mills and optionally the addition of surfactants, as have already been listed e.g. above for the other types of formulation.

Emulsions, e.g. oil-in-water emulsions (EW), can be prepared, for example, by means of stirrers, colloid mills and/or static mixers using aqueous organic solvents and optionally surfactants, as have already been listed e.g. above for the other formulation types.

Granules can be prepared either by spraying the active ingredient onto adsorptive granular inert material or by applying active ingredient concentrates to the surface of carriers, such as sand, kaolinites or granular inert material, by means of adhesives, for example polyvinyl alcohol, sodium polyacrylate or else mineral oils. Suitable active ingredients can also be granulated in the manner customary for producing fertilizer granules—if desired in a mixture with fertilizers.

Water-dispersible granules are usually produced by the customary processes such as spray-drying, fluidized-bed granulation, pan granulation, mixing with high-speed mixers and extrusion without solid inert material.

For the production of pan, fluidized-bed, extruder and spray granules, see e.g. processes in "Spray Drying Handbook" 3rd Ed. 1979, G. Goodwin Ltd., London, J. E. Browning, "Agglomeration", Chemical and Engineering 1967, pages 147 ff, "Perry's Chemical Engineers Handbook", 5th Ed., McGraw Hill, New York 1973, p. 857.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical preparations generally comprise 0.1 to 99% by weight, in particular 0.1 to 95% by weight, of compounds according to the invention.

In wettable powders, the active ingredient concentration is e.g. about 10 to 90% by weight, the remainder to 100% by weight consists of customary formulation constituents. In the case of emulsifiable concentrations, the active ingredient concentration can be about 1 to 90, preferably 5 to 80% by weight. Dust-type formulations contain 1 to 30% by weight of active ingredient, preferably at most 5 to 20% by weight of active ingredient, sprayable solutions comprise about 0.05 to 80, preferably 2 to 50% by weight of active ingredient. In the case of water-dispersible granules, the active ingredient content depends partially on whether the active compound is present in liquid or solid form and on which granulation auxiliaries, fillers, etc., are used. In the water-dispersible granules, the content of active ingredient is, for example, between 1 and 95% by weight, preferably between 10 and 80% by weight.

In addition, the specified active ingredient formulations optionally comprise the adhesives, wetting agents, dispersants, emulsifiers, penetration agents, preservatives, frost protection agents and solvents, fillers, carriers and dyes, antifoams, evaporation inhibitors and agents influencing the pH and viscosity customary in each case.

On the basis of these formulations, it is also possible to produce combinations with other pesticidally active substances, for example insecticides, acaricides, herbicides, fungicides, and also with safeners, fertilizers and/or growth regulators, for example in the form of a finished formulation or as a tankmix.

For application, the formulations in commercial form are, if appropriate, diluted in a customary manner, for example in the case of wettable powders, emulsifiable concentrates, dispersions and water-dispersible granules with water. Dust-type preparations, granules for soil application or granules for scattering and sprayable solutions are not normally diluted further with other inert substances prior to application.

The required application rate of the compounds of the formula (I) varies with the external conditions, including temperature, humidity and the type of herbicide used. It can vary within wide limits, for example between 0.001 and 1.0 kg/ha or more of active substance, but it is preferably between 0.005 and 750 g/ha.

The examples below additionally illustrate the present invention.

A. Chemical Examples

Example D3: 3-[2,6-Dimethyl-4-(prop-1-yn-1-yl)phenyl]-4-hydroxy-7-propoxy-1-azaspiro[4.5]dec-3-en-2-one

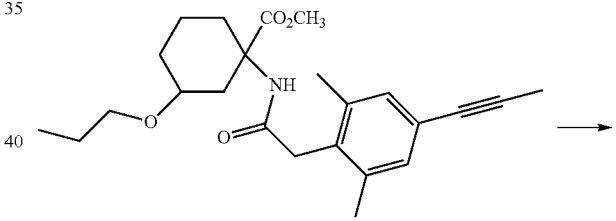

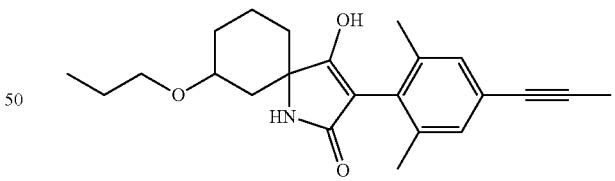

1.50 g (3.75 mmol) of methyl 1-({[2,6-dimethyl-4-(prop-1-yn-1-yl)phenyl]acetyl}amino)-3-propoxycyclohexanecarboxylate in 10 ml of DMF were added dropwise over 30 min at room temperature to a solution of 1.05 g of potassium t-butoxide (9.2 mmol) in 5 ml of DMF and stirred overnight at this temperature. The mixture was added to ice-water, acidified to pH 1 with 2N hydrochloric acid and the precipitate that precipitates was filtered under suction. After drying, this gave 1.18 g (86%) of the title compound in the form of colorless crystals with m.p. 219° C.

TABLE 7

Example numbers D1-D14
Analogously to Example D3 and also according to the general details relating to the production, the following compounds according to the invention were obtained.

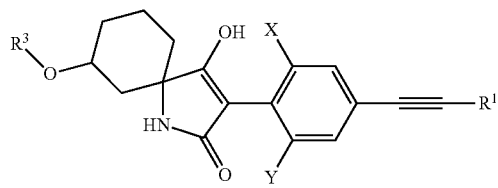

| Example No. | $R^3$ | X | Y | $R^1$ | $^1$H-NMR [400 MHz, δ in ppm, $d_6$-DMSO] or melting point [° C.] |
|---|---|---|---|---|---|
| D1 | $C_2H_5$ | $C_2H_5$ | $C_2H_5$ | $CH_3$ | m.p. 235° C. |
| D2 | $C_2H_5$ | $CH_3$ | $CH_3$ | $CH_3$ | m.p. 285° C. |
| D3 | n-$C_3H_7$ | $CH_3$ | $CH_3$ | $CH_3$ | m.p. 219° C. |
| D4 | n-$C_4H_9$ | $CH_3$ | $CH_3$ | H | m.p. 135-136° C. |
| D5 | —$CH_2CH_2OCH_3$ | $C_2H_5$ | $C_2H_5$ | $CH_3$ | δ = 1.01 (mc, 6H), 1.55-1.80 (m, 4H), 2.02 (s, 3H), 2.37 (mc, 4H), 3.25 (s, 3H), 3.41 (mc, 2H), 3.48-3.61 (m, 3H), 7.05 (s, 2H) |
| D6 | —$CH_2CH_2OCH_3$ | $CH_3$ | $CH_3$ | $CH_3$ | δ = 1.08 (mc, 1H) 1.30 (mc, 1H), 1.58-1.82 (m, 4H), 2.02 (mc, 9H), 3.24 (s, 3H), 3.41 (mc, 2H), 3.52 (mc, 2H), 3.57 (mc, 1H), 7.05 (s, 2H) |
| D7 | —$CH_2CH_2OCH_3$ | H | $C_2H_5$ | $CH_3$ | |
| D8 | —$CH_2CH_2OCH_3$ | $CH_3$ | $C_2H_5$ | $CH_3$ | δ = 1.00 (mc, 3H), 2.05 (s, 3H), 2.40 (mc, 2H), 3.25 (s, 3H), 3.40 (mc, 2H), 3.47-3.62 (m, 3H), 7.05 (s, 1H), 7.07 (s, 1H) |
| D9 | —$CH_2CH_2OCH_3$ | $CH_3$ | $C_2H_5$ | H | δ = 1.02 (mc, 3H), 1.60-1.88 (m, 5H), 2.05 and 2.08 (each s, Σ3H), 2.43 (mc, 2H), 3.22 (s, 3H), 3.40-3.62 (m, 3H), 4.08 (s, 1H), 7.13 (s, 1H), 7.16 (s, 1H) |
| D10 | —$CH_2CH_2OCH_3$ | $C_2H_5$ | $C_2H_5$ | H | δ = 1.05 (mc, 6H), 2.40 (mc, 4H), 3.24 (s, 3H), 3.41 (mc, 2H), 3.45-3.65 (m, 3H), 4.09 (s, 1H), 7.15 (s, 2H) |
| D11 | n-$C_3H_7$ | $C_2H_5$ | $CH_3$ | $CH_3$ | δ = 0.86 (t, 3H), 1.02 (t, 3H), 1.09 (mc, 1H), 1.29 (mc, 1H), 1.48 (quint., 2H), 2.02 (s, 3H), 2.40 (mc, 2H), 3.55 (mc, 1H), 7.06 (s, 1H), 7.07 (s, 1H) |
| D12 | n-$C_3H_7$ | $C_2H_5$ | $C_2H_5$ | $CH_3$ | |
| D13 | n-$C_3H_7$ | $CH_3$ | $CH_3$ | H | δ = 1.31 (mc, 2H), 2.08 (s, 3H), 2.11 (s, 3H), 3.25 (s, 3H), 3.40 (mc, 2H), 3.52 (mc, 2H), 3.59 (mc, 1H), 4.09 (s, 1H), 7.15 (s, 2H) |
| D14 | n-$C_3H_7$ | $CH_3$ | $C_2H_5$ | H | |

Example P7: 3-(4-Ethynyl-2,6-diethylphenyl)-4-hydroxy-7-(2-methoxyethoxy)-1-azaspiro[4.5]dec-3-en-2-one

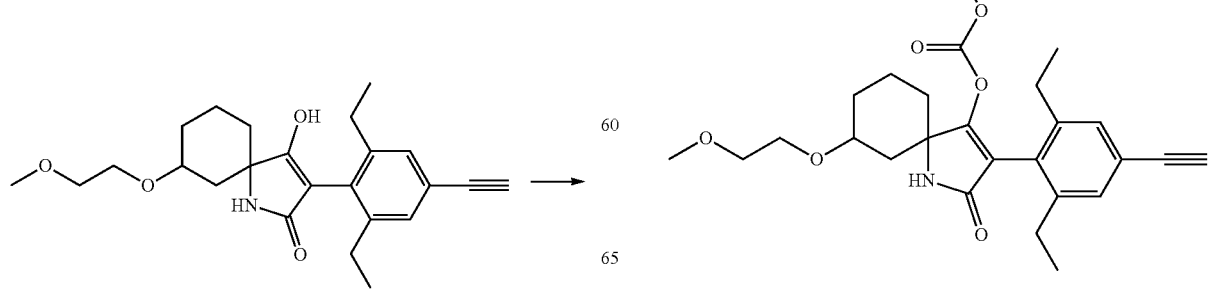

176 mg g (0.44 mmol) of 3-(4-ethynyl-2,6-diethylphenyl)-4-hydroxy-8-methoxy-1-aza-spiro[4.5]dec-3-en-2-one were initially charged with 0.5 ml of triethylamine in 8 ml of dichloromethane and the mixture was stirred at 40° C. for 10 minutes. 58 mg (0.53 mmol) of ethyl chloroformate in 3 ml of dichloromethane were then slowly added dropwise and the mixture left to stir at room temperature for 3 h. After washing with 10 ml of sodium hydrogen carbonate solution and 10 ml of water, drying (magnesium sulfate) and distilling off the solvent, the crude product was purified by column chromatography on silica gel (ethyl acetate/n-heptane). 70 mg (33%) of the title compound was thus obtained as a colorless solid.

TABLE 8

Example numbers P1-P23
Analogously to Example P7 and according to the general details relating to the production, the following compounds according to the invention are obtained:

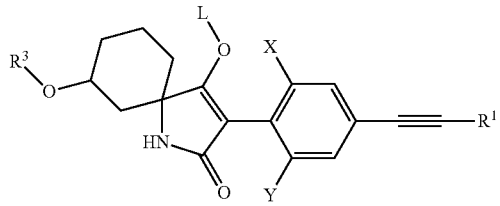

| Example No. | $R^3$ | X | Y | $R^1$ | L | $^1$H-NMR [400 MHz, δ in ppm, CDCl$_3$] or melting point [° C.] |
|---|---|---|---|---|---|---|
| P1 | $C_2H_5$ | $C_2H_5$ | $CH_3$ | $CH_3$ | $CO_2C_2H_5$ | |
| P2 | $C_2H_5$ | $C_2H_5$ | $C_2H_5$ | $CH_3$ | $CO_2C_2H_5$ | |
| P3 | $C_2H_5$ | $C_2H_5$ | $C_2H_5$ | $CH_3$ | COiPr | m.p. 206° C. |
| P4 | $C_2H_5$ | $C_2H_5$ | $C_2H_5$ | $CH_3$ | $CO_2C_2H_5$ | m.p. 202° C. |
| P5 | n-$C_4H_9$ | $CH_3$ | $CH_3$ | H | $CO_2C_2H_5$ | m.p. 173° C. |
| P6 | n-$C_4H_9$ | $CH_3$ | $CH_3$ | H | COiPr | m.p. 208° C. |
| P7 | —$CH_2CH_2OCH_3$ | $C_2H_5$ | $C_2H_5$ | H | $CO_2C_2H_5$ | δ = 1.15 (mc, 9H), 1.80 (mc, 2H), 1.99 (mc, 2H), 2.20 (mc, 2H), 2.52 (mc, 4H), 3.05 (s, 1H) , 3.38 (s, 3H), 3.46 (mc, 1H), 3.52 (mc, 2H), 4.02 (q, 2H), 7.23 (s, 2H) |
| P8 | —$CH_2CH_2OCH_3$ | $C_2H_5$ | $C_2H_5$ | H | COiPr | δ = 0.98 (d, 3H), 1.18 (mc, 6H), 2.45-2.60 (m, 5H), 3.04 (s, 1H), 3.38 (s, 3H), 3.48 (mc, 1H), 3.51 (mc, 2H), 3.56-3.70 (m, 2H), 7.22 (s, 2H) |
| P9 | —$CH_2CH_2OCH_3$ | $CH_3$ | $C_2H_5$ | H | $CO_2C_2H_5$ | δ = 1.10-1.19 (mc, 6H), 1.72-1.88 (m, 2H), 1.90-2.05 (m, 2H), 2.50 (mc, 2H), 3.38 (s, 3H), 3.52 (mc, 2H), 4.01 (q, 2H), |
| P10 | —$CH_2CH_2OCH_3$ | $CH_3$ | $C_2H_5$ | H | COiPr | δ = 0.98 (mc, 6H), 1.15 (mc, 3H), 1.90-2.05 (m, 2H), 2.19 and 2.22 (each s, Σ3H), 2.50 (mc, 3H), 3.02 (s, 1H), 3.39 (s, 3H), 3.40-3.72 (m, 5H) |
| P11 | $CH_2CH_2OCH_3$ | $CH_3$ | $CH_3$ | H | $CO_2C_2H_5$ | δ = 1.12 (t, 3H), 1.80 (mc, 2H), 1.99 (mc, 2H), 2.19 (s, 3H), 2.21 (s, 3H), 3.02 (s, 1H), 3.38 (s, 3H), 3.48 (mc, 1H), 3.51 (mc, 2H), 3.63 (mc, 2H), 4.02 (q, 2H), 7.22 (s, 1H), 7.24 (s, 1H) |
| P12 | $CH_2CH_2OCH_3$ | $C_2H_5$ | $C_2H_5$ | $CH_3$ | COiPr | δ = 0.97 (d, 6H), 1.12 (mc, 6H), 2.05 (s, 3H), 2.49 (mc, 2H), 3.38 (s, 3H), 3.45 (mc, 1H), 3.52 (mc, 2H), 3.48-3.70 (m, 2H), 7.12 (s, 2H) |
| P13 | $CH_2CH_2OCH_3$ | $CH_3$ | $C_2H_5$ | $CH_3$ | $CO_2C_2H_5$ | δ = 1.10-1.18 (mc, 6H), 2.02 (s, 3H), 2.48 (mc, 2H), 3.38 (s, 3H), 4.02 (q, 2H), 7.10 (mc, 2H) |
| P14 | $CH_2CH_2OCH_3$ | $CH_3$ | $CH_3$ | $CH_3$ | $CO_2$iPr | δ = 1.08 (mc, 6H), 2.00 (s, 3H), 2.18 (mc, 6H), 3.47 (s, 3H), 3.43 (mc, 1H), 3.51 mc, 2H), 3.62 (mc, 2H), 4.62 (mc, 1H), 7.07 (s, 2H) |
| P15 | $CH_2CH_2OCH_3$ | $CH_3$ | $CH_3$ | $CH_3$ | $CO_2C_2H_5$ | δ = 1.12 (t, 3H), 2.02 (s, 3H), 2.18 (mc, 6H), 3.38 (s, 3H), 3.43 (mc, 1H), 3.51 (mc, 2H), 3.62 (mc, 2H), 4.00 (q, 2H), 7.08 (s, 2H) |
| P16 | $CH_2CH_2OCH_3$ | $CH_3$ | $CH_3$ | $CH_3$ | $CO_2CH_3$ | δ = 1.23 (mc, 2H), 1.48 (mc, 2H), 1.79 (mc, 2H), and 1.99 (mc, 2H), 2.02 (s, 3H), 2.18 (mc, 6H), 3.38 (s, 3H), 3.47 (mc, 1H), 3.51 (mc, 2H), 3.58 (s, 3H), 3.55-3.70 (m, 2H), 7.08 (s, 2H) |
| P17 | $CH_2CH_2OCH_3$ | $CH_3$ | $CH_3$ | H | COiPr | δ = 1.00 (d, 6H), 1.91-2.05 (m, 2H), 2.19 (s, 3H), 2.21 (s, 3H), 2.52 (hept., 1H), 3.01 (s, 1H), 3.38 (s, 3H), 3.45 (mc, 1H), 3.51 (mc, 2H), 3.63 (mc, 2H), 7.18 (s, 2H) |
| P18 | n-$C_3H_7$ | $CH_3$ | $CH_3$ | $CH_3$ | $CO_2CH_3$ | |
| P19 | n-$C_3H_7$ | $CH_3$ | $C_2H_5$ | $CH_3$ | $CO_2C_2H_5$ | |
| P20 | n-$C_3H_7$ | $CH_3$ | $C_2H_5$ | $CH_3$ | $CO_2C_2H_5$ | |
| P21 | n-$C_3H_7$ | $CH_3$ | $C_2H_5$ | $CH_3$ | COiPr | δ = 0.89-1.02 (m, 6H), 1.12 (mc, 3H), 2.02 (s, 3H), 2.18 and 2.20 (each s, Σ3H), 2.40-2.58 (m, 2H), 3.35-3.49 (m, 2H), 7.09 (s, 1H), 7.11 (s, 1H) |
| P22 | n-$C_3H_7$ | $C_2H_5$ | $C_2H_5$ | $CH_3$ | $CO_2C_2H_5$ | |
| P23 | n-$C_3H_7$ | $C_2H_5$ | $C_2H_5$ | $CH_3$ | COiPr | |

Preparation Examples (Starting Materials)

Example G24: Methyl 1-({[2-ethyl-6-methyl-4-(prop-1-yn-1-yl)phenyl]acetyl}amino)-3-(2-methoxyethoxy)cyclohexanecarboxylate

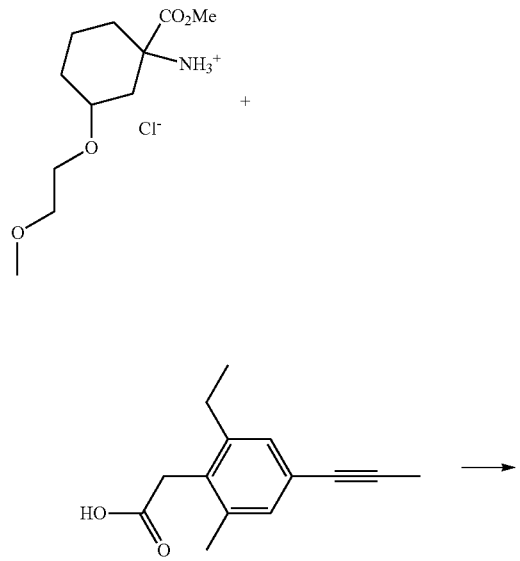

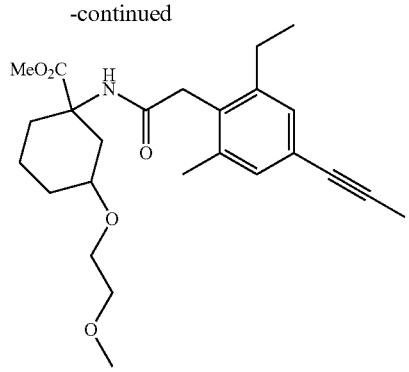

1.00 g (4.6 mmol) of 2-ethyl-6-methyl-4-propynylphenylacetic acid were dissolved in 25 ml of dichloromethane and admixed with one drop of DMF. 1.25 g (9.88 mmol) of oxalyl chloride were added and the mixture was heated under reflux to boiling until gas stopped evolving. Then, the reaction solution was concentrated, admixed twice more with in each case 30 ml of dichloromethane and concentrated again in order finally to take up the residue in 4 ml of dichloromethane (solution 1). 1.33 g (5 mmol) of cis-3-methoxyethoxy-1-(methoxycarbonyl)cyclohexanaminium chloride and 1 g of triethylamine were dissolved in 20 ml of dichloromethane and solution 1 was added dropwise over the course of 90 min. After stirring for 18 h, the mixture was admixed with 50 ml of water, and the organic phase was separated off, concentrated and purified by column chromatography (silica gel, gradient ethyl acetate/n-heptane). This gave 1.71 g (87%) of the desired precursor.

TABLE 9

Example numbers G1-G30
Analogously to Example G24 and according to the general details relating to the production, the following compounds are obtained:

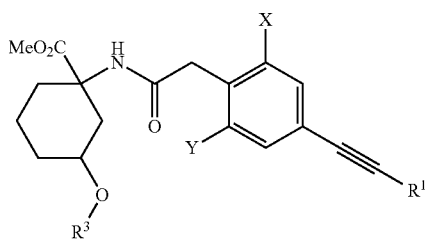

| Ex. No. | $R^3$ | X | Y | $R^1$ | $^1$H-NMR (400 MHz, δ in ppm, CDCl$_3$) or melting point |
|---|---|---|---|---|---|
| G1 | CH$_3$ | CH$_3$ | CH$_3$ | H | |
| G2 | CH$_3$ | C$_2$H$_5$ | CH$_3$ | H | |
| G3 | CH$_3$ | C$_2$H$_5$ | C$_2$H$_5$ | H | |
| G4 | CH$_3$ | CH$_3$ | CH$_3$ | CH$_3$ | |
| G5 | CH$_3$ | C$_2$H$_5$ | CH$_3$ | CH$_3$ | |
| G6 | CH$_3$ | C$_2$H$_5$ | C$_2$H$_5$ | CH$_3$ | |
| G7 | C$_2$H$_5$ | CH$_3$ | CH$_3$ | H | |
| G8 | C$_2$H$_5$ | CH$_3$ | C$_2$H$_5$ | H | |
| G9 | C$_2$H$_5$ | C$_2$H$_5$ | C$_2$H$_5$ | H | |
| G10 | C$_2$H$_5$ | CH$_3$ | CH$_3$ | CH$_3$ | m.p. 158° C. |
| G11 | C$_2$H$_5$ | CH$_3$ | C$_2$H$_5$ | CH$_3$ | |
| G12 | C$_2$H$_5$ | C$_2$H$_5$ | C$_2$H$_5$ | CH$_3$ | |
| G13 | n-C$_3$H$_7$ | CH | CH | H | |
| G14 | n-C$_3$H$_7$ | C$_2$H$_5$ | CH$_3$ | H | |
| G15 | n-C$_3$H$_7$ | C$_2$H$_5$ | C$_2$H$_5$ | H | |
| G16 | n-C$_3$H$_7$ | CH | CH | CH | m.p. 145° C. |
| G17 | n-C$_3$H$_7$ | CH$_3$ | C$_2$H$_5$ | CH$_3$ | |
| G18 | n-C$_3$H$_7$ | C$_2$H$_5$ | C$_2$H$_5$ | CH | |
| G19 | CH$_2$CH$_2$OCH$_3$ | CH$_3$ | CH$_3$ | H | |
| G20 | CH$_2$CH$_2$OCH$_3$ | C$_2$H$_5$ | CH$_3$ | H | |
| G21 | CH$_2$CH$_2$OCH$_3$ | C$_2$H$_5$ | C$_2$H$_5$ | H | |

TABLE 9-continued

Example numbers G1-G30
Analogously to Example G24 and according to the general details relating to the production, the following compounds are obtained:

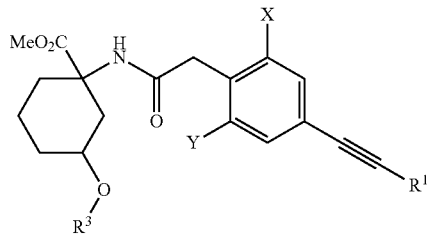

| Ex. No. | R³ | X | Y | R¹ | ¹H-NMR (400 MHz, δ in ppm, CDCl₃) or melting point |
|---|---|---|---|---|---|
| G22 | CH₂CH₂OCH₃ | C₂H₅ | C₂H₅ | CH₃ | δ = 1.22 (mc, 6H), 2.62 (mc, 2H), 3.35 (s, 3H), 3.68 (s, 2H), 7.20 (s, 2H) |
| G23 | CH₂CH₂OCH₃ | CH₃ | CH₃ | CH₃ | δ = 2.01 (s, 3H), 2.33 (s, 6H), 3.47 (s, 3H), 3.53-3.70 (m, 3H), 3.70 (s, 2H), 7.07 (s, 2H) |
| G24 | CH₂CH₂OCH₃ | CH₃ | C₂H₅ | CH₃ | δ = 1.21 (t, 3H), 2.05 (s, 3H), 2.18 (s, 3H), 2.52 (q, 2H), 3.37 (s, 3H), 3.48 (mc, 4H), 3.62 (s, 2H), 7.17 (s, 1H), 7.19 (s, 1H) |
| G25 | n-C₄H₉ | CH₃ | CH₃ | H | m.p. 154-155° C. |
| G26 | n-C₄H₉ | C₂H₅ | CH₃ | H | |
| G27 | n-C₄H₉ | C₂H₅ | C₂H₅ | H | |
| G28 | n-C₄H₉ | CH₃ | CH₃ | CH₃ | |
| G29 | n-C₄H₉ | CH₃ | C₂H₅ | CH₃ | |
| G30 | n-C₄H₉ | C₂H₅ | C₂H₅ | CH₃ | |

B. Formulation Examples a) A dusting product is obtained by mixing 10 parts by weight of a compound of the formula (I) and/or salts thereof and 90 parts by weight of talc as inert substance and comminuting the mixture in an impact mill.

b) A readily water-dispersible, wettable powder is obtained by mixing 25 parts by weight of a compound of the formula (I) and/or salts thereof, 64 parts by weight of kaolin-containing quartz as inert substance, 10 parts by weight of potassium ligninosulphonate and 1 part by weight of sodium oleoylmethyltaurate as wetting agent and dispersant and grinding in a pinned-disc mill.

c) A readily water-dispersible dispersion concentrate is obtained by mixing 20 parts by weight of a compound of the formula (I) and/or salts thereof with 6 parts by weight of alkylphenol polyglycol ether (®Triton X 207), 3 parts by weight of isotridecanol polyglycol ether (8 EO) and 71 parts by weight of paraffinic mineral oil (boiling range e.g. about 255 to more than 277° C.) and grinding to a fineness of below 5 microns in an attrition ball mill.

d) An emulsifiable concentrate is obtained from 15 parts by weight of a compound of the formula (I) and/or salts thereof, 75 parts by weight of cyclohexanone as solvent and 10 parts by weight of oxethylated nonylphenol as emulsifier.

e) Water-dispersible granules are obtained by mixing
75 parts by weight of a compound of the formula (I) and/or salts thereof,
10 parts by weight of calcium ligninosulphonate,
5 parts by weight of sodium laurylsulphate,
3 parts by weight of polyvinyl alcohol and
7 parts by weight of kaolin,
grinding the mixture in a pinned-disc mill, and granulating the powder in a fluidized bed by spray application of water as a granulating liquid.

f) Water-dispersible granules are also obtained by homogenizing and precomminuting
25 parts by weight of a compound of the formula (I) and/or salts thereof,
5 parts by weight of sodium 2,2' dinaphthylmethane-6,6' disulphonate,
2 parts by weight of sodium oleoylmethyltaurate,
1 part by weight of polyvinyl alcohol,
17 parts by weight of calcium carbonate and
50 parts by weight of water on a colloid mill,
then grinding the mixture in a bead mill and atomizing and drying the resulting suspension in a spray tower by means of a one-phase nozzle.

C. Biological Data

1. Pre-Emergence Herbicidal Effect

Seeds of monocotyledonous and dicotyledonous weed plants and crop plants are laid out in wood-fibre pots in sandy loam and covered with soil. The compounds according to the invention formulated in the form of wettable powders (WP) or as emulsion concentrates (EC) are then applied as aqueous suspension or emulsion at a water application rate of 600 to 800 l/ha (converted) with the addition of 0.2% wetting agent to the surface of the covering soil.

After the treatment, the pots are placed in a greenhouse and kept under good growth conditions for the trial plants. The damage to the test plants is scored visually after a test period of 3 weeks by comparison with untreated controls (herbicidal activity in percent (%): 100% activity=the plants have died, 0% activity=like control plants).

Undesired Plants/Weeds:

| | | | |
|---|---|---|---|
| ALOMY: | *Alopecurus myosuroides* | SETVI: | *Setaria viridis* |
| AMARE: | *Amaranthus retroflexus* | AVEFA: | *Avena fatua* |
| CYPES: | *Cyperus esculentus* | ECHCG: | *Echinochloa crus-galli* |
| LOLMU: | *Lolium multiflorum* | STEME: | *Stellaria media* |
| VERPE: | *Veronica persica* | VIOTR: | *Viola tricolor* |
| POLCO: | *Polygonum convolvulus* | | |

TABLE 10

Pre-emergence effects

| Example No. | Dosage [g a.i./ha] | ALOMY | AVEFA | CYPES | ECHCG | LOLMU | SETVI |
|---|---|---|---|---|---|---|---|
| D1 | 320 | 100 | 100 | | 100 | 100 | 100 |
| | 80 | 100 | 80 | | 100 | 100 | 100 |
| D2 | 320 | 100 | 100 | | 100 | 100 | 100 |
| | 80 | 100 | 80 | | 100 | 100 | 100 |
| D3 | 320 | 100 | 100 | | 100 | 100 | 100 |
| | 80 | 100 | 80 | | 100 | 100 | 100 |
| D4 | 320 | | | 100 | 100 | 80 | 80 |
| | 80 | | | | | | |
| D5 | 320 | 100 | 100 | | 100 | 100 | 100 |
| | 80 | 100 | 100 | | 100 | 100 | 100 |
| D6 | 320 | 100 | 100 | 90 | 100 | 100 | 100 |
| | 80 | 100 | 100 | | 100 | 100 | 100 |
| D7 | 320 | 100 | 100 | | 100 | 100 | 100 |
| | 80 | 100 | | | 100 | 100 | 100 |
| D8 | 320 | 100 | 100 | 100 | 100 | 100 | 100 |
| | 80 | 100 | 100 | | 100 | 100 | 100 |
| D10 | 320 | 100 | 100 | | 100 | | 100 |
| | 80 | 90 | 90 | | 100 | | 100 |
| P1 | 320 | 100 | 100 | 100 | 100 | 100 | 100 |
| | 80 | 100 | 80 | 100 | 100 | 100 | 100 |
| P2 | 320 | 100 | 100 | | 100 | 100 | 100 |
| | 80 | 100 | 100 | | 100 | 100 | 100 |
| P3 | 320 | 100 | 80 | | 100 | 100 | 100 |
| | 80 | 90 | | | 100 | 100 | 100 |
| P4 | 320 | 100 | 100 | | 100 | 100 | 100 |
| | 80 | 100 | 100 | | 100 | 100 | 100 |
| P5 | 320 | 100 | 80 | | 100 | 100 | 100 |
| | 80 | 80 | | | 90 | 90 | 90 |
| P6 | 320 | 80 | | | 90 | 100 | 100 |
| | 80 | | | | | | |
| P12 | 320 | 100 | 100 | | 100 | 100 | 100 |
| | 80 | 100 | 100 | | 100 | 100 | 100 |
| P13 | 320 | 100 | 100 | 90 | 100 | 100 | 100 |
| | 80 | 100 | 100 | | 100 | 100 | 100 |
| P14 | 320 | 100 | 100 | | 100 | 100 | 100 |
| | 80 | 100 | 100 | | 100 | 100 | 100 |
| P15 | 320 | 100 | 100 | | 100 | 100 | 100 |
| | 80 | 100 | 100 | | 100 | 100 | 100 |
| P16 | 320 | 100 | 100 | | 100 | 100 | |
| | 80 | 100 | 100 | | 100 | 100 | |

As the results from Table 10 show, the compounds according to the invention have a good herbicidal pre-emergence effectiveness against a broad spectrum of weed grasses and weeds. For example, the compounds D1-D8, D10, P1-P6 and P12-P16 at an application rate of 320 g a.i./ha in each case exhibit an 80-100% effect against *Alopecurus myosuroides*, *Avena fatua*, *Echinochloa crus-galli*, *Lolium multiflorum* and *Setaria viridis*. Accordingly, the compounds according to the invention are suitable for controlling unwanted plant growth by the pre-emergence method.

2. Post-Emergence Herbicidal Effect

Seeds of monocotyledonous and dicotyledonous weed and crop plants are laid out in sandy loam in wood-fibre pots, covered with soil and cultivated in a greenhouse under good growth conditions. 2 to 3 weeks after sowing, the test plants are treated at the one-leaf stage. The compounds according to the invention, formulated in the form of wettable powders (WP) or as emulsion concentrates (EC), are then sprayed as aqueous suspension or emulsion at a water application rate of 600 to 800 l/ha (converted) with the addition of 0.2% of wetting agent onto the green parts of the plants. After the test plants have been left to stand in the greenhouse under optimal growth conditions for about 3 weeks, the action of the preparations is assessed visually in comparison to untreated controls (herbicidal action in percent (%): 100% activity=the plants have died, 0% activity=like control plants).

TABLE 11

Post-emergence effects

| Example No. | Dosage [g a.i./ha] | ALOMY | AVEFA | ECHCG | LOLMU | SETVI | AMARE | POLCO |
|---|---|---|---|---|---|---|---|---|
| D1 | 80 | 100 | | 100 | 90 | 100 | | |
| | 20 | 80 | | 100 | | 90 | | |
| D2 | 80 | 90 | | 100 | 100 | 90 | | |
| | 20 | | | 90 | | | | |

TABLE 11-continued

| | | Post-emergence effects |||||||
|---|---|---|---|---|---|---|---|---|
| Example | Dosage | Herbicidal effect against [%] |||||||
| No. | [g a.i./ha] | ALOMY | AVEFA | ECHCG | LOLMU | SETVI | AMARE | POLCO |
| D3 | 80 | | 90 | 100 | 100 | 100 | 90 | |
| | 20 | | | 100 | 80 | 80 | | |
| D5 | 80 | 100 | 100 | 100 | 100 | 100 | | |
| | 20 | 100 | 100 | 100 | 100 | 100 | | |
| D6 | 80 | 100 | 100 | 100 | 100 | 100 | 80 | 80 |
| | 20 | 100 | 100 | 100 | 100 | 100 | 80 | |
| D7 | 80 | 100 | 100 | 100 | 100 | 100 | | |
| | 20 | 100 | 100 | 100 | 100 | 100 | | |
| D8 | 80 | 100 | 100 | 100 | 100 | 100 | | |
| | 20 | 100 | 100 | 100 | 100 | 100 | | |
| D10 | 80 | 90 | 90 | 90 | | | | |
| | 20 | 90 | 80 | 90 | | | | |
| P1 | 80 | | | | | 100 | | |
| | 20 | | | | | | | |
| P2 | 80 | | | 80 | | | | |
| | 20 | | | | | | | |
| P3 | 80 | | | 90 | | | | |
| | 20 | | | | | | | |
| P4 | 80 | 100 | 100 | 100 | 100 | 100 | 80 | |
| | 20 | | | 100 | 100 | 100 | | |
| P12 | 80 | 100 | 100 | 100 | 100 | 100 | | |
| | 20 | 100 | 100 | 100 | 100 | 100 | | |
| P13 | 80 | 100 | 100 | 100 | 100 | 100 | | |
| | 20 | 100 | 100 | 100 | 100 | 100 | | |
| P14 | 80 | 100 | 90 | 100 | 100 | 100 | | |
| | 20 | 100 | 90 | 100 | 100 | 90 | | |
| P15 | 80 | 100 | 100 | 100 | 100 | 100 | 80 | 80 |
| | 20 | 100 | 100 | 100 | 100 | 100 | 80 | |
| P16 | 80 | 100 | 100 | 100 | 100 | 100 | 80 | |
| | 20 | 100 | 100 | 100 | 100 | 100 | 80 | |

As the results from Table 11 show, the compounds according to the invention have a good herbicidal post-emergence effectiveness against a broad spectrum of weed grasses and weeds. For example, the compounds D1-D8, D10, P1-P4 and P12-P16 and at an application rate of 80 g/ha in each case exhibit an 80-100% effect against *Alopecurus myosuroides, Avena fatua, Echinochloa crus-galli, Lolium multiflorum* and *Setaria viridis*. Accordingly, the compounds according to the invention are suitable for controlling unwanted plant growth by the post-emergence method.

The invention claimed is:

1. An alkynyl-substituted N-phenylpyrrolidine-2,4-dione of formula (I)

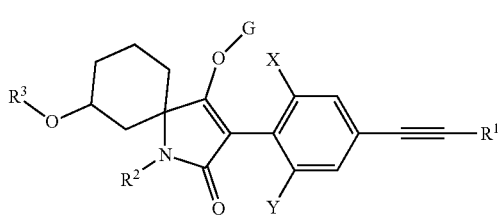

or a salt thereof, wherein
X is methyl, ethyl or cyclopropyl,
Y is methyl or ethyl,
$R^1$ is methyl,
$R^2$ is hydrogen,
$R^3$ is $C_1$-$C_6$-alkyl or $C_1$-$C_4$-alkoxy-$C_2$-$C_4$-alkyl,
G is hydrogen, a cleavable group L or a cation E, where
  L is one of the following radicals

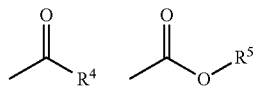

wherein
$R^4$ is methyl, ethyl or isopropyl,
$R^5$ is isopropyl, methyl or ethyl, and
E is a sodium, potassium, trimethylammonium, pyridinium, quinolinium or trimethylsulphonium cation or an ion equivalent of calcium or magnesium.

2. The alkynyl-substituted N-phenylpyrrolidine-2,4-dione of formula (I) according to claim 1, wherein $R^3$ is $C_1$-$C_4$-alkyl or $C_1$-$C_3$-alkoxy-$C_2$-$C_4$-alkyl.

3. An herbicidal composition comprising the alkynyl-substituted N-phenylpyrrolidine-2,4-dione of formula (I) according to claim 1 or an agrochemically acceptable salt thereof, and optionally an agrochemically acceptable carrier, diluent and/or solvent.

4. The herbicidal composition according to claim 3, comprising at least one further agrochemically active substance selected from the group consisting of insecticides, acaricides, herbicides, fungicides, safeners and growth regulators.

5. The herbicidal composition according to claim 4, comprising a safener.

6. The herbicidal composition according to claim 3, comprising a further herbicide.

7. A method of controlling undesired plant growth comprising applying the alkynyl-substituted N-phenylpyrrolidine-2,4-dione of formula (I) according to claim 1 to the plant to be controlled, a part of the plant to be controlled, a seed of the plant to be controlled or to soil in which undesired plant growth could take place.

8. The method according to claim 7, wherein the undesired plant is a monocotyledonous weed.

9. The method according to claim 7, wherein the undesired plant is a grass resistant to (a) one or more herbicides inhibiting acetyl-CoA-carboxylase, (b) glyphosate, and/or (c) one or more herbicides inhibiting acetolactate synthase, and wherein the grass is in a crop of a useful plant.

10. The method according to claim 9, wherein the useful plant is selected from the group consisting of wheat, barley, rye, oats, rice, sugar cane, soybean, rapeseed, sunflower and corn.

11. The alkynyl-substituted N-phenylpyrrolidine-2,4-dione of formula (I) or an agrochemically acceptable salt thereof according to claim 1, wherein
G is E.

12. The alkynyl-substituted N-phenylpyrrolidine-2,4-dione of formula (I) or a salt thereof according to claim 1, wherein G is hydrogen.

13. The alkynyl-substituted N-phenylpyrrolidine-2,4-dione of formula (I) or a salt thereof according to claim 1, wherein $R^3$ is $C_1$-$C_4$-alkoxy-$C_2$-$C_4$-alkyl.

\* \* \* \* \*